United States Patent [19]

Shizgal

[11] Patent Number: 4,911,175
[45] Date of Patent: Mar. 27, 1990

[54] METHOD FOR MEASURING TOTAL BODY CELL MASS AND TOTAL EXTRACELLULAR MASS BY BIOELECTRICAL RESISTANCE AND REACTANCE

[75] Inventor: Harry Shizgal, Dollard Des Orneaux, Canada

[73] Assignees: Diana Twyman, Birmingham; Rudolph J. Liedtke, Detroit, both of Mich.; part interest to each

[21] Appl. No.: 98,009

[22] Filed: Sep. 17, 1987

[51] Int. Cl.[4] .............................................. A61B 5/05
[52] U.S. Cl. ..................................... 128/734; 128/774
[58] Field of Search ............... 128/734, 741, 630, 632, 128/693, 774

[56] References Cited

U.S. PATENT DOCUMENTS

| Re. 30,101 | 9/1979 | Kubicek . | |
|---|---|---|---|
| 3,316,896 | 5/1967 | Thomasset | 128/734 |
| 3,320,946 | 5/1967 | Dethloff et al. | 128/734 |
| 3,340,867 | 9/1967 | Kubicek et al. . | |
| 3,452,743 | 7/1969 | Rieke . | |
| 3,730,171 | 5/1973 | Namon . | |
| 3,735,247 | 5/1973 | Harker | 128/774 X |
| 3,742,936 | 7/1973 | Blanie . | |
| 3,786,349 | 1/1974 | Devenyi . | |
| 3,851,641 | 12/1974 | Toole . | |
| 3,871,359 | 3/1975 | Pacela . | |
| 3,874,368 | 4/1975 | Asrican . | |
| 3,909,709 | 9/1975 | Maxon . | |
| 3,949,736 | 4/1976 | Vrana et al. . | |
| 3,971,365 | 7/1976 | Smith . | |
| 4,008,712 | 2/1977 | Nyboer . | |
| 4,071,820 | 1/1978 | Mushinsky . | |
| 4,116,231 | 9/1978 | Matsuo . | |
| 4,240,443 | 12/1980 | Ionescu | 128/734 |
| 4,387,723 | 6/1983 | Atlee, III et al. | 128/734 |
| 4,437,469 | 3/1984 | Djordjevich et al. | 128/672 |
| 4,450,527 | 5/1984 | Sramek | 364/415 |

OTHER PUBLICATIONS

Article entitled "Total Body Potassium In Surgical Patients" from *Surgery* publication, Jun., 1974, vol. 73, No. 6, pp. 900–907 by H. M. Shizgal and Robert S. Kurtz and Douglas Wood.

Article entitled "Body Composition Of Patients With Malnutrition and Cancer" from *Cancer* publication, Jan. 1 Supplement, 1985, from the Dept. of Surgery, McGill Univ., Royal Victoria Hospital Montreal, Quebec, Canada by Harry M. Shizgal, M.D.

Article entitled "Theory and Validation of the Tetrapolar Bioelectrical Impedance Method To Assess Human Body Composition" from the International Symposium on In Vivo Body Composition Studies, Brookhaven National Laboratory, Upton, Long Island, N.Y. Sep. 28–Oct. 1, 1986 by H. C. Lukaski and W. W. Bolonchuk.

Article entitled "Assessment of Fat-Free Mass Using Bioelectrical Impedance Measurements of the Human Body" from The American Journal of Clinical Nutrition, Apr. 1985 by H. C. Lukaski, P. E. Johnson, W. W. Bolonchuk and G. I. Lykken.

(List continued on next page.)

*Primary Examiner*—Angela D. Sykes
*Attorney, Agent, or Firm*—Basile and Hanlon

[57] ABSTRACT

A method for measuring total body cell mass, total body extracellular mass, total exchangeable potassium and total exchangeable sodium of a subject by using bioelectrical resistance and reactance. The method includes the steps of connecting electrodes attached to an electrical impedance analyzer to the subject followed by introducing a high frequency, low amperage current through the electrodes into the body of the subject. The bioelectrical resistance and reactance of the subject are then measured by the impedance analyzer. Finally, the total body cell mass, total extracellular mass, total exchangeable potassium and the total exchangeable sodium of the subject are determined by applying the measured resistance and reactance to equations derived from multiple linear regression analysis of total body resistance and reactance of a selected group of subjects.

6 Claims, 1 Drawing Sheet

OTHER PUBLICATIONS

Article entitled "Validation of Tetrapolar Bioelectrical Impedance Method To Assess Human Body Composition" from United States Dept. of Agriculture, Agricultural Research Service, Sep. 12, 1985 by H. C. Lukaski, W. W. Bolonchuk, C. B. Hall and W. A. Siders.

Article entitled "Estimation of Total Body Water By Bioelectrical Impedance Analysis" from The American Journal of Clinical Nutrition, Sep. 1986, by R. F. Kushner and D. A. Schoeller.

Article entitled "Body Composition Measurements From Whole Body Resistance and Reactance" from the Department of Surgery McGill Univ. at Royal Victoria Hospital, Montreal, Quebec, Canada by D. McDougall and H. M. Shizgal, 1981.

METHOD FOR MEASURING TOTAL BODY CELL MASS AND TOTAL EXTRACELLULAR MASS BY BIOELECTRICAL RESISTANCE AND REACTANCE

BACKGROUND OF THE INVENTION

1. Field of the Invention

This invention relates to methods for determining body composition from the electrical characteristics of the body and, more specifically, to methods for measuring body cell mass, extracellular mass, total exchangeable potassium and total exchangeable sodium from total body electrical resistance and reactance.

2. Description of the Prior Art

A variety of techniques and devices have been devised to measure the various components of body composition such as body fat, lean body mass, body cell mass and extracellular mass in humans and animals as a means of assessing their nutritional status and general health.

Particular interest has been directed to body cell mass which is the potassium rich, energy exchanging component of the body responsible for all metabolic activity and extracellular mass which is the nonliving component of the body composed of water and extracellular solids, such as bone, collagen and adipose, is metabolically inactive, does not consume any oxygen and serves mainly support and transport functions.

Malnutrition is characterized by a loss of body cell mass, accompanied by an expansion of the extracellular mass. When a malnourished state is corrected with the appropriate nutritional support the reverse occurs; the body cell mass increases, while there is an accompanying contraction of the extracellular mass. Body cell mass contains 98–99% of all total body potassium. The intracellular potassium concentration of the body is fairly constant thus resulting in a very close relationship between total body potassium and body cell mass. Further, since the majority of the body's sodium is in the extracellular mass, there is a close relationship between total exchangeable sodium and the total extracellular mass. However, because some of the sodium in bone is fixed within the bone matrix and does not exchange with injected isotopes of sodium, total body sodium and total exchangeable sodium are significantly different. As a result the ratio of total exchangeable sodium divided by the total exchangeable potassium, which is a measure of the extracellular mass expressed as a function of the body cell mass, is a sensitive measure of the nutritional state of a patient.

The measurement of body cell mass and extracellular mass requires specialized and expensive instrumentation or invasive techniques. Body cell mass has been determined by measuring the total body content of 40K, the naturally occurring radioactive isotope of potassium. 40K comprises 0.0118% of all naturally occurring potassium and is measured using expensive total body counter equipment which must be constructed with special steel, and which requires difficult calibration.

Another approach which has been employed to measure the body cell mass is isotope dilution. Two techniques have been established. The first involves injecting 42K, a short lived radioactive isotope of potassium. Twenty four hours following the isotope injection, blood samples are obtained and from the specific activity of 42K, the body cell mass is determined. Because 42K has a very short half life of 12.4 hours, its routine use is extremely difficult, except as a research tool. An alternate technique has been developed to measure both the body cell mass and the extracellular mass. This technique employes the simultaneous intravenous injection of 22Na, a radioactive isotope of sodium, and 3H2O, water labeled with a radioactive isotope of hydrogen. This technique avoids the difficulty associated with short lived radioactive isotopes. However, both techniques suffer from the need to inject radioactive substances, thus exposing the subjects to radiation. With both techniques urine and blood samples must be obtained during the 24 hours following the administration of isotopes. Thus at least 24 hours are required to obtain a single measurement. Furthermore, repeated measurements within a few days are difficult to obtain.

These methods or techniques also suffer from other problems such as:

1. They are invasive, i.e., radioactive isotopes or other toxic substances are injected into the patient for subsequent measurement.
2. The patient is subject to external characteristics, such as renal function defects, which effect the overall measurement of the injected substance.
3. Blood and other in vivo tissues may be required for subsequent analysis.
4. There is a considerable length of time required to obtain the required samples for subsequent data analysis.
5. Repetition of the process may be difficult within a short period of time.
6. Such processes have been expensive in terms of the number of expendable supplies, laboratory personnel, tracer substances and tissue assays utilized.

Thus, it would be desirable to provide a method for measuring total body cell mass and total extracellular mass of a subject which overcomes the above-listed problems. It would also be desirable to provide a method for measuring total body cell mass and total extracellular mass which is simple, non-invasive, inexpensive, accurate and can be repeated often. Finally, it would be desirable to provide a method for measuring total body cell mass and total extracellular mass which is non-invasive, i.e., does not require the injection of potentially toxic or harmful substances into the body or the sampling of either blood or other tissue and fluids.

SUMMARY OF THE INVENTION

The present invention is a method for measuring total body cell mass and total extracellular mass, and also total exchangeable potassium (which is equivalent to total body potassium) and total exchangeable sodium from total body electrical resistance and reactance measurements.

The method includes the step of attaching an impedance plethysmograph to the patient. Preferably, the plethysmograph is a four terminal impedance, phase sensitive device in which the four terminals or electrodes are attached to various portions of the patient. Next, a high frequency, low amperage current is introduced into the body.

As the high frequency, low amperage current is introduced, the total body electrical resistance and reactance of the patient are measured and displayed on the plethysmograph. Finally, the total body cell mass, total extracellular mass, total exchangeable potassium and total exchangeable sodium are determined by using the measured total body resistance and reactance and other data, such as height of the patient, in equations derived from statistical (multiple linear regression) analysis of body composition data of selected test groups.

This new method solves many of the problems associated with previously available techniques used to measure the constituents of body composition. The new method is simple, quick, non-invasive, can be repeated as often as desired, and does not require specialized personnel, expensive and complex equipment or the taking of blood and tissue samples from the subject.

BRIEF DESCRIPTION OF THE DRAWING

The various features, advantages and other uses of the present invention will become more apparent by referring to the following detailed description and drawing in which.

DESCRIPTION OF THE PREFERRED EMBODIMENTS

Figure 2:
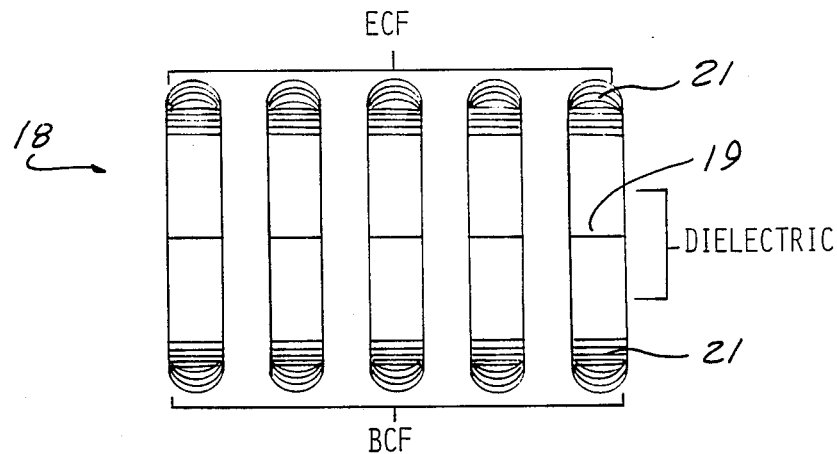
FIG. 2 is a pictorial representation of a typical cell membrane showing the cell membrane as a capacitor between the extracellular and intracellular spaces.

Throughout the following description and drawing, an identical reference number is used to refer the same component shown in multiple figures of the drawing.

Before explaining the present invention in its best mode, a general explanation of concepts regarding body compositions will be furnished to provide a clearer understanding of this invention.

Figure 1:
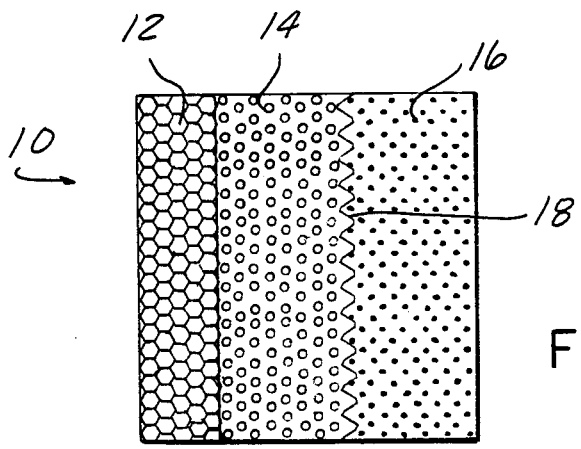
FIG. 1 is a cross-section of a typical body cell area showing the three main constituents of body composition; namely, extracellular mass, body cell mass, and body fat.

Total body mass, which is equivalent to body wight, is the sum of body fat and the lean body mass. The lean body mass is composed of two major components, namely, body cell mass and extracellular mass. The body cell mass, reference number 14 in FIG. 1, is a component of body tissue which is rich in potassium, and performs energy exchanging and work performing functions. The body cell mass (BCM) 14 includes all of the intracellular fluids and solids and is surrounded by a semi-permeable cell membrane and the body fat layers 12. By contrast, the extracellular mass (ECM) 16 which includes all of the extracellular water and solids, such as bone and collagen, is metabolically inactive, and does not perform work, consume oxygen or produce carbon dioxide. The BCM 14 and ECM 16 are separated by a semi-permeable cell membrane 18.

The impedance of a body (human or animal) can be determined through the conduction of an electrical current through the organism. A living organism consists of intra and extracellular fluids that behave an electrical conductors and cell membranes which act as electrical capacitors as shown in FIG. 2, in the human body. The cell membrane 18 consists of a layer 19 of non-conductive, lipid substance sandwiched between two layers 21 of conductive polar molecules.

Electrical resistance is the measure of the voltage drop of an electrical current as it passes through a resistive substance. In biologically intact tissues, resistance is lowest in lean tissues with a high water content and quantity of conducting electrolytes and higher in dry, non-conductive tissues, with high contents of solids and fat, such as adipose and bone, and low contents of water.

Reactance is the measure of the out-of-phase voltage in a circuit of parallel and series resistors and capacitors through which alternating current flows. In the human body, the cell membrane 18, as shown in FIG. 2, consists of a layer 19 of a non-conductive lipid or fatty substance disposed between two layers 21 of conductive, polar molecules. The human body is comprised of intracellular and extracellular fluids separated by these semi-permeable cell membranes 18. The intra and extracellular fluids act as electrical conductors while the cell membranes 18 with the electrical characteristics of capacitors behave as electrically reactive components.

Thus, reactance is a measure of the quantity of cell membrane capacitance and serves as an indication of thre quantity of intracellular or body cell mass. Body fat, total body water and extracellular water offer only resistance to electrical current whereas cell membranes offer only reactance.

Phase angle, expressed in degrees, is the arc tangent of reactance over resistance. In a population of healthy subjects with a normal body composition, phase angle varies from 4 to 15 degrees. Lower phase angles are consistent with lower reactances arising because of a breakdown of the semipermeable cell membrane as occurs with cell death. Higher phase angles represent an increased cell membrane reactance and, therefore, a larger proportion of body cell mass.

METHOD

The present method of measuring certain constituents of body composition, namely, total body cell mass and total extracellular mass, requires the measurement of bioelectrical resistance and reactance of a subject followed by the application of the measured resistance and reactance to a set of equations developed from multiple linear regression analysis of body composition data obtained from a large group of subjects.

Figure 3:
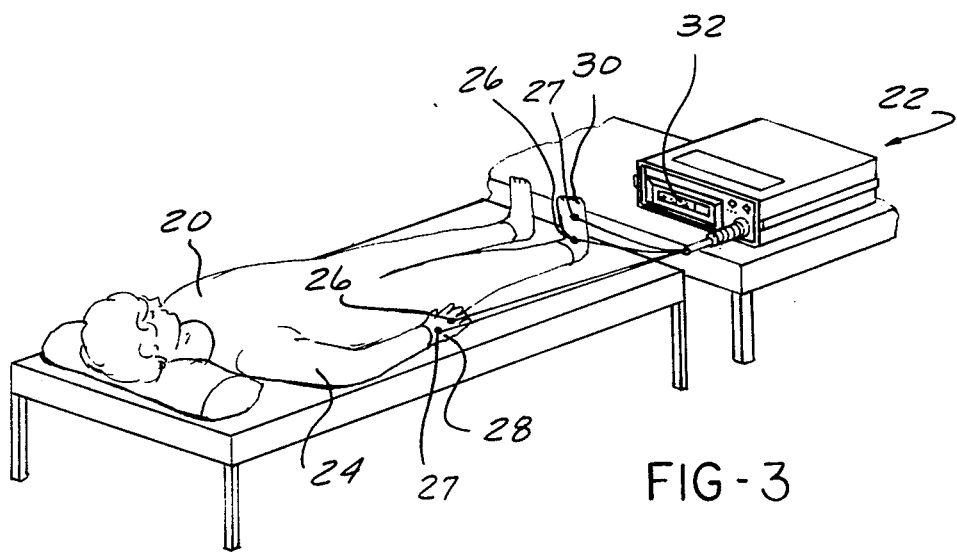
FIG. 3 is a pictorial representation of a patient attached to an impedance plethysmograph used in the method of the present invention.

The first step in the present method involves connecting a conventional electrical impedance analyzer 22, such as a four terminal or electrode, phase sensitive, impedance plethysmograph as shown in FIG. 3, to the subject 20. The subject 20 is typically in a prone position with the arms 24 placed so they do not touch the torso. Conductive spot electrodes 26 and 27 attached to the terminals of the plethysmograph 22 are placed on the dorsal surfaces of one hand 28 and one foot 30, respectively, on either the right or left side, either both on the same side or on opposite sides of the body.

A current is passed between one set of electrodes (the current electrodes) while the other set of electrodes (the sensing electrodes) detects the voltage drop therebetween. The electrodes 26 and 27 on the hand 28 are placed such that the sensing electrode 26 is positioned on the dorsal surface of the hand 28 between the prominences of the radius and ulna; while the current electrode 27 is also on the dorsal surface but over the metacarpals. Two electrodes 26 and 27 are positioned on the dorsal surface of the foot 30 with the current electrode 27 attached over the distal end of the metatarsals and the sensing electrode 26 placed between the lateral and medial malleola. This is by way of example only since other electrode confirmations may also be used with the present technique.

Next, an excitation current is applied between the two current electrodes 27 and introduced into the subject 20. By way of example only and not limitation, a current of 800 microamperes at 50 KHz is introduced into the current electrodes 27 on the hand 28 and foot 30. The voltage drop is detected by the impedance analyzer 22 across the proximal or sensing electrodes 26 attached to the hand 28 and foot 30. The impedance analyzer 22 measures the whole body resistance and reactance as well as the phase angle and outputs such measured values on a visible display 32. It should be noted that any frequency other than that described above may be used in the present invention as long as the impedance can still be accurately measured in separate vectors of resistance and reactance.

The final step in the present method is determining the body cell mass, the total extracellular mass, the total exchangeable potassium and the total exchangeable sodium by applying the measured resistance and reactance along with other data, such as the height of the subject, to equations derived from statistical (multiple linear regression) analysis of measured bioelectrical resistance and reactance data from selected test groups obtained by other measurement techniques, such as isotope dilution.

For purposes of this invention, bioelectrical resistance and reactance were measured in four test groups of subjects by isotope dilution as shown in Table 1 (9 normally nourished females), Table 2 (14 normally nourished males), Table 3 (23 malnourished females) and Table 4 (18 malnourished males). From this test data, a number of equations for determining total body cell mass, total extracellular mass, total exchangeable potassium and total exchangeable sodium were derived using standard multiple linear regression analysis techniques. Accordingly:

$$LBM = 16.4 + 0.61(H_t)^2/R \quad [1]$$

Where:
LBM = lean body mass (kg)
$H_t$ = height (cm)
R = total body resistance (ohms)

$$ECM/BCM = 2.4 + 34.8/X_c - 5.97 \times 10^{-5}(H_t)^2 \quad [2]$$

Where:
ECM = extracellular mass (kg)
BCM = body cell mass (kg)
$X_c$ = total body reactance (ohms)

$$LBM = ECM + BCM \quad [3]$$

Combining equations 1, 2 and 3

$$BCM = \frac{16.4 + 0.61(H_t)^2/R}{3.4 + 34.8/X_c - 5.97 \times 10^{-5}(H_t)^2} \quad [4]$$

$$ECM = 16.4 + 0.61(H_t)^2/R - \quad [5]$$

$$\frac{16.4 + 0.61(H_t)^2/R}{3.4 + 34.8/X_c - 5.97 \times 10^{-5}(H_t)^2}$$

These equations, which show a high degree of correlation with the test data, can be used to determine certain constituents of the body composition of a subject simply by applying the measured bioelectrical resistance and reactance and the height of the subject thereto and thereby provide a general indication of the state of health of the subject.

Similarly derived equations for total exchangeable potassium and sodium can also be generated from the test data as follows:

$$K_e = \frac{1968 + 7.32(H_t)^2/R}{3.4 + 34.8/X_c - 5.97 \times 10^{-5}(H_t)^2} \quad [6]$$

Where:
$K_e$ = total exchangeable potassium (mEq)

$$Na_e/K_e = 1.87 + 34.1/X_c - 4.66 \times 10^{-5}(H_t)^2 \quad [7]$$

Where:
$Na_e$ = total exchangeable sodium (mEq)

$$Na_e = (1.87 + 34.1/X_c - 4.66 \times 10^{-5}(H_t)^2)/K_e \quad [8]$$

Equations 6, 7 and 8 can be used to indicate the general state of health of the subject since total exchangeable potassium and total exchangeable sodium are substantially identical to total body cell mass and total extracellular mass, respectively.

Thus, the present invention provides a direct and non-invasive method for measuring total body cell mass, total extracellular mass, total exchangeable potassium and total exchangeable sodium of a subject through the simple process of attaching four electrodes connected to an impedance plethysmograph to various portions of the subject's body and measuring the bioelectrical resistance and reactance of the subject generated by passing a harmless, high frequency, low amperage electrical current through the body.

In summary, there has been disclosed a unique method for determining certain constituents of body compositions, such as, total body cell mass, extracellular mass, total exchangeable potassium and total exchangeable sodium by non-invasive measurement of bioelectrical resistance and reactance. This new technique can be repeated quickly and as many times as desired without harm to the subject and without undue expense in terms of specially trained personnel or expensive, complex equipment. There is also the advantage of nonuse of radioactive tracers or other toxic substances as required in previous measurement techniques.

TABLE 1

| | | | | | | Normally Nourished Females | | | | | | | | | |
|---|---|---|---|---|---|---|---|---|---|---|---|---|---|---|---|
| Subject | Sex | Age yr | TBW L | $Na_e$ mEq | $K_e$ mEq | $Na_e$/TBW mEq/L | $K_e$/TBW mEg/L | $Na_e$/$K_e$ | BCM Kg | LBM Kg | BODY FAT Kg | ECM Kg | Resist | React | Height cm | Weight Kg |
| 1 | F | 48 | 48.9 | 3507 | 4122 | 71.7 | 84.3 | 0.85 | 34.3 | 67.0 | 28.7 | 32.7 | 450 | 50 | 182.9 | 95.9 |
| 2 | F | 61 | 34.2 | 2554 | 2778 | 74.7 | 81.3 | 0.92 | 23.1 | 46.8 | 6.7 | 23.7 | 656 | 48 | 160.0 | 53.5 |
| 3 | F | 27 | 27.5 | 1954 | 2289 | 71.0 | 83.2 | 0.85 | 19.1 | 37.7 | 9.3 | 18.6 | 767 | 81 | 157.5 | 47.0 |
| 4 | F | 63 | 26.9 | 2252 | 1923 | 83.6 | 71.4 | 1.17 | 16.0 | 36.9 | 20.1 | 20.9 | 716 | 58 | 160.0 | 57.0 |
| 5 | F | 19 | 31.3 | 2282 | 2416 | 73.0 | 77.3 | 0.94 | 20.1 | 42.8 | 12.5 | 22.7 | 646 | 77 | 167.6 | 55.5 |
| 6 | F | 27 | 26.1 | 2114 | 1922 | 80.8 | 73.5 | 1.10 | 16.0 | 35.8 | 9.5 | 19.8 | 796 | 79 | 157.5 | 45.4 |
| 7 | F | 30 | 42.4 | 3475 | 2978 | 81.9 | 70.2 | 1.17 | 24.8 | 58.1 | 3.1 | 33.3 | 522 | 38 | 176.5 | 61.2 |

TABLE 1-continued

Normally Nourished Females

| Subject | Sex | Age yr | TBW L | $Na_e$ mEq | $K_e$ mEq | $Na_e$/TBW mEq/L | $K_e$/TBW mEq/L | $Na_e$/$K_e$ | BCM Kg | LBM Kg | BODY FAT Kg | ECM Kg | Resist | React | Height cm | Weight Kg |
|---|---|---|---|---|---|---|---|---|---|---|---|---|---|---|---|---|
| 8 | F | 57 | 25.8 | 2051 | 1709 | 79.4 | 66.1 | 1.20 | 14.2 | 35.4 | 20.1 | 21.2 | 793 | 84 | 162.6 | 55.5 |
| 9 | F | 29 | 32.9 | 2420 | 2621 | 73.6 | 79.8 | 0.92 | 21.8 | 45.0 | 23.0 | 23.2 | 633 | 57 | 167.6 | 68.0 |
| Mean | | 40.1 | 32.9 | 2512 | 2529 | 76.7 | 76.3 | 1.01 | 21.1 | 45.1 | 14.8 | 24.0 | 664.3 | 63.6 | 165.8 | 59.9 |
| SEM | | 5.7 | 2.7 | 195 | 244 | 1.6 | 2.1 | 0.05 | 2.0 | 3.7 | 2.8 | 1.8 | 39.9 | 5.6 | 3.0 | 5.0 |

TBW = total body water, $Na_e$ = total exchangeable sodium, $K_e$ = total exchangeable potassium, BCM = body cell mass, LBM = lean body mass, ECM = extracellular mass, Resist = total body bioelectrical resistance, React = total body bioelectrical reactance

TABLE 2

Normally Nourished Males

| Subject | Sex | Age yr | TBW L | $Na_e$ mEq | $K_e$ mEq | $Na_e$/TBW mEq/L | $K_e$/TBW mEq/L | $Na_e$/$K_e$ | BCM Kg | LBM Kg | BODY FAT Kg | ECM Kg | Resist | React | Height cm | Weight Kg |
|---|---|---|---|---|---|---|---|---|---|---|---|---|---|---|---|---|
| 1 | M | 57 | 38.1 | 2822 | 3014 | 74.0 | 79.0 | 0.94 | 25.1 | 52.3 | 9.7 | 27.1 | 587 | 56 | 180.3 | 62.0 |
| 2 | M | 60 | 39.2 | 3002 | 2795 | 76.6 | 71.3 | 1.07 | 23.3 | 53.7 | 9.0 | 30.4 | 488 | 40 | 165.1 | 62.7 |
| 3 | M | 52 | 39.7 | 2794 | 3359 | 70.5 | 84.7 | 0.83 | 28.0 | 54.3 | 41.8 | 26.3 | 580 | 69 | 188.0 | 96.4 |
| 4 | M | 34 | 40.4 | 2528 | 3508 | 62.6 | 86.9 | 0.72 | 29.2 | 55.3 | 2.7 | 26.1 | 537 | 57 | 180.3 | 58.0 |
| 5 | M | 57 | 39.1 | 3040 | 2735 | 77.8 | 70.0 | 1.11 | 22.8 | 53.5 | 11.5 | 30.8 | 551 | 50 | 180.3 | 65.0 |
| 6 | M | 37 | 48.4 | 3713 | 3921 | 76.7 | 81.0 | 0.95 | 32.7 | 66.3 | 15.3 | 33.6 | 420 | 46 | 177.8 | 81.7 |
| 7 | M | 25 | 38.3 | 2739 | 3314 | 71.5 | 86.4 | 0.83 | 27.6 | 52.5 | 13.3 | 24.9 | 533 | 56 | 177.8 | 65.8 |
| 8 | M | 46 | 33.6 | 2516 | 2550 | 74.8 | 75.8 | 0.99 | 21.2 | 46.1 | 19.7 | 24.8 | 765 | 58 | 177.8 | 65.9 |
| 9 | M | 66 | 31.9 | 2501 | 2140 | 78.4 | 67.1 | 1.17 | 17.8 | 43.7 | 18.0 | 25.9 | 708 | 45 | 154.9 | 61.8 |
| 10 | M | 23 | 35.1 | 2599 | 2913 | 73.9 | 82.9 | 0.89 | 24.3 | 48.1 | 9.0 | 23.9 | 610 | 55 | 182.9 | 57.2 |
| 11 | M | 63 | 56.5 | 4068 | 4465 | 72.0 | 79.1 | 0.91 | 37.2 | 77.4 | 28.1 | 40.2 | 313 | 37 | 174.0 | 105.5 |
| 12 | M | 60 | 46.1 | 3421 | 3538 | 74.2 | 76.8 | 0.97 | 29.5 | 63.1 | 32.1 | 33.7 | 496 | 55 | 180.3 | 95.5 |
| 13 | M | 57 | 42.6 | 2920 | 3776 | 68.5 | 88.6 | 0.77 | 31.5 | 58.4 | 30.2 | 26.9 | 605 | 73 | 185.4 | 88.6 |
| 14 | M | 26 | 41.0 | 2728 | 3781 | 66.5 | 92.1 | 0.72 | 31.5 | 56.2 | 7.3 | 24.7 | 479 | 71 | 177.8 | 63.6 |
| Mean | | 47.4 | 40.7 | 2957 | 3272 | 72.7 | 80.1 | 0.92 | 27.3 | 55.8 | 17.7 | 28.5 | 548.0 | 54.9 | 177.3 | 73.5 |
| SEM | | 4.1 | 1.7 | 126 | 166 | 1.2 | 2.0 | 0.04 | 1.4 | 2.3 | 3.0 | 1.2 | 30.1 | 2.9 | 2.2 | 4.4 |

TBW = total body water, $Na_e$ = total exchangeable sodium, $K_e$ = total exchangeable potassium, BCM = body cell mass, LBM = lean body mass, ECM = extracellular mass, Resist = total body bioelectrical resistance, React = total body bioelectrical reactance

TABLE 3

Malnourished Females

| Subject | Sex | Age yr | TBW L | $Na_e$ mEq | $K_e$ mEq | $Na_e$/TBW mEq/L | $K_e$/TBW mEq/L | $Na_e$/$K_e$ | BCM Kg | LBM Kg | BODY FAT Kg | ECM Kg | Resist | React | Height cm | Weight Kg |
|---|---|---|---|---|---|---|---|---|---|---|---|---|---|---|---|---|
| 1 | F | 63 | 30.1 | 2665 | 1793 | 88.7 | 59.7 | 1.49 | 14.9 | 41.2 | 10.3 | 26.2 | 696 | 41 | 154.9 | 51.5 |
| 2 | F | 31 | 29.3 | 2433 | 1778 | 83.1 | 60.7 | 1.37 | 14.8 | 40.1 | 13.0 | 25.3 | 672 | 46 | 154.9 | 53.2 |
| 3 | F | 30 | 32.2 | 2808 | 2039 | 87.2 | 63.4 | 1.38 | 17.0 | 44.1 | 13.1 | 27.1 | 629 | 66 | 176.5 | 57.2 |
| 4 | F | 76 | 26.2 | 2652 | 1354 | 101.1 | 51.6 | 1.96 | 11.3 | 35.9 | 29.8 | 24.7 | 596 | 56 | 165.1 | 65.9 |
| 5 | F | 76 | 29.9 | 2991 | 1438 | 100.0 | 48.1 | 2.08 | 12.0 | 41.0 | 31.4 | 29.0 | 559 | 33 | 165.1 | 72.4 |
| 6 | F | 70 | 33.6 | 3737 | 1390 | 111.4 | 41.4 | 2.69 | 11.6 | 46.0 | 4.0 | 34.4 | 399 | 19 | 157.5 | 51.0 |
| 7 | F | 73 | 22.4 | 2160 | 1239 | 96.4 | 55.3 | 1.74 | 10.3 | 30.7 | 9.8 | 20.4 | 792 | 42 | 152.4 | 40.5 |
| 8 | F | 85 | 32.5 | 3124 | 1719 | 96.2 | 52.9 | 1.82 | 14.3 | 44.5 | 22.9 | 30.2 | 547 | 31 | 157.5 | 67.5 |
| 9 | F | 76 | 29.3 | 2817 | 1373 | 96.1 | 46.8 | 2.05 | 11.4 | 40.2 | 22.8 | 28.7 | 483 | 27 | 165.1 | 63.6 |
| 10 | F | 43 | 37.0 | 3145 | 2342 | 85.1 | 63.3 | 1.34 | 19.5 | 50.6 | 0.9 | 31.1 | 564 | 32 | 170.2 | 51.5 |
| 11 | F | 85 | 31.7 | 2888 | 1812 | 91.0 | 57.1 | 1.59 | 15.1 | 43.5 | 23.8 | 28.4 | 587 | 36 | 157.5 | 67.3 |
| 12 | F | 75 | 24.5 | 2092 | 1539 | 85.3 | 62.7 | 1.36 | 12.8 | 33.6 | 14.0 | 20.8 | 883 | 49 | 162.6 | 47.7 |
| 13 | F | 31 | 34.2 | 2870 | 1888 | 84.0 | 55.2 | 1.52 | 15.7 | 46.8 | 4.4 | 31.1 | 805 | 53 | 154.9 | 51.3 |
| 14 | F | 63 | 37.0 | 3850 | 1758 | 104.0 | 47.5 | 2.19 | 14.6 | 50.7 | 9.3 | 36.1 | 582 | 35 | 154.9 | 60.0 |
| 15 | F | 73 | 21.0 | 1762 | 1281 | 83.8 | 60.9 | 1.38 | 10.7 | 28.8 | 10.5 | 18.1 | 1046 | 72 | 152.4 | 39.3 |
| 16 | F | 31 | 25.3 | 2288 | 1604 | 90.5 | 63.5 | 1.43 | 13.4 | 34.6 | 15.0 | 21.3 | 671 | 49 | 154.9 | 49.5 |
| 17 | F | 64 | 30.8 | 2752 | 2017 | 89.3 | 65.4 | 1.36 | 16.8 | 42.2 | 19.0 | 25.4 | 624 | 54 | 170.2 | 61.4 |
| 18 | F | 66 | 32.8 | 2919 | 2101 | 89.0 | 64.1 | 1.39 | 17.5 | 44.9 | 50.8 | 27.4 | 473 | 46 | 162.6 | 95.9 |
| 19 | F | 37 | 36.2 | 3236 | 2093 | 89.3 | 57.8 | 1.55 | 17.4 | 49.6 | 40.9 | 32.2 | 482 | 26 | 162.6 | 90.5 |
| 20 | F | 58 | 35.4 | 3023 | 2323 | 85.4 | 65.6 | 1.30 | 19.3 | 48.5 | 50.0 | 29.1 | 425 | 46 | 157.5 | 98.6 |
| 21 | F | 37 | 39.1 | 3424 | 2237 | 87.6 | 57.3 | 1.53 | 18.6 | 53.5 | 37.0 | 34.9 | 509 | 31 | 162.6 | 90.5 |
| 22 | F | 78 | 24.4 | 2163 | 1463 | 88.5 | 59.9 | 1.48 | 12.2 | 33.5 | 32.9 | 21.3 | 636 | 33 | 152.4 | 66.4 |
| 23 | F | 43 | 25.1 | 3116 | 2112 | 124.3 | 84.2 | 1.48 | 17.6 | 34.3 | 17.7 | 16.7 | 539 | 32 | 165.1 | 52.0 |
| Mean | | 59.3 | 30.4 | 2822 | 1769 | 92.9 | 58.5 | 1.63 | 14.7 | 41.7 | 21.0 | 27.0 | 617.3 | 41.5 | 160.4 | 62.8 |
| SEM | | 4.0 | 1.0 | 107 | 72 | 2.1 | 1.8 | 0.07 | 0.6 | 1.4 | 2.9 | 1.1 | 31.6 | 2.7 | 1.4 | 3.5 |

TBW = total body water, $Na_e$ = total exchangeable sodium, $K_e$ = total exchangeable potassium, BCM = body cell mass, LBM = lean body mass, ECM = extracellular mass, Resist = total body bioelectrical resistance, React = total body bioelectrical reactance

TABLE 4

Malnourished Males

| Subject | Sex | Age yr | TBW L | $Na_e$ mEq | $K_e$ mEq | $Na_e$/TBW mEq/L | $K_e$/TBW mEq/L | $Na_e$/$K_e$ | BCM Kg | LBM Kg | BODY FAT Kg | ECM Kg | Resist | React | Height cm | Weight Kg |
|---|---|---|---|---|---|---|---|---|---|---|---|---|---|---|---|---|
| 1 | M | 69 | 48.6 | 5005 | 2550 | 103.0 | 52.5 | 1.96 | 21.2 | 66.6 | 9.4 | 45.3 | 401 | 18 | 172.7 | 76.0 |

TABLE 4-continued

| | | | | | | Nae/ | | | | | BODY | | | | | |
|---|---|---|---|---|---|---|---|---|---|---|---|---|---|---|---|---|
| | | | | | | | | | | | Malnourished Males | | | | | |
| Subject | Sex | Age yr | TBW L | Nae mEq | Ke mEq | TBW mEq/L | Ke/TBW mEq/L | Nae/ Ke | BCM Kg | LBM Kg | FAT Kg | ECM Kg | Resist | React | Height cm | Weight Kg |
| 2 | M | 50 | 29.6 | 2664 | 1896 | 90.1 | 64.1 | 1.40 | 15.8 | 40.5 | 20.0 | 24.7 | 613 | 41 | 165.1 | 60.5 |
| 3 | M | 86 | 33.2 | 2887 | 2340 | 87.0 | 70.5 | 1.23 | 19.5 | 45.4 | 10.6 | 25.9 | 608 | 37 | 175.3 | 56.0 |
| 4 | M | 69 | 51.0 | 5381 | 2308 | 105.5 | 45.2 | 2.33 | 19.2 | 69.9 | 8.1 | 50.6 | 350 | 18 | 170.2 | 78.2 |
| 5 | M | 74 | 31.0 | 2994 | 1806 | 96.4 | 58.2 | 1.66 | 15.0 | 42.5 | 13.5 | 27.5 | 513 | 40 | 170.2 | 56.0 |
| 6 | M | 60 | 34.5 | 2879 | 2250 | 83.4 | 65.2 | 1.28 | 18.7 | 47.3 | 12.7 | 28.5 | 543 | 63 | 165.1 | 60.0 |
| 7 | M | 79 | 34.3 | 3823 | 1450 | 111.3 | 42.2 | 2.64 | 12.1 | 47.0 | 1.0 | 35.0 | 622 | 27 | 157.5 | 48.0 |
| 8 | M | 44 | 40.8 | 3502 | 2593 | 85.9 | 63.6 | 1.35 | 21.6 | 55.9 | 29.1 | 34.3 | 471 | 52 | 180.3 | 85.0 |
| 9 | M | 65 | 39.8 | 3989 | 2193 | 100.2 | 55.1 | 1.82 | 18.3 | 54.6 | 8.5 | 36.3 | 389 | 31 | 162.6 | 63.2 |
| 10 | M | 70 | 48.2 | 5878 | 2122 | 122.0 | 44.0 | 2.77 | 17.7 | 66.0 | 9.3 | 48.3 | 393 | 24 | 172.7 | 52.7 |
| 11 | M | 60 | 31.9 | 2674 | 2029 | 83.8 | 63.6 | 1.32 | 16.9 | 43.7 | 12.8 | 26.8 | 577 | 69 | 157.5 | 52.0 |
| 12 | M | 74 | 29.8 | 2791 | 1827 | 93.7 | 61.4 | 1.53 | 15.2 | 40.8 | 16.1 | 25.6 | 612 | 31 | 170.2 | 56.9 |
| 13 | M | 78 | 33.7 | 3115 | 1660 | 92.5 | 49.3 | 1.88 | 13.8 | 46.1 | 11.2 | 32.3 | 541 | 31 | 172.7 | 57.3 |
| 14 | M | 74 | 32.0 | 3082 | 1985 | 96.3 | 62.0 | 1.55 | 16.5 | 43.8 | 12.2 | 27.3 | 575 | 25 | 170.2 | 56.0 |
| 15 | M | 70 | 30.1 | 2572 | 1936 | 85.4 | 64.3 | 1.33 | 16.1 | 41.3 | 9.7 | 25.1 | 626 | 42 | 167.6 | 51.0 |
| 16 | M | 74 | 28.1 | 2560 | 2041 | 91.0 | 72.6 | 1.25 | 17.0 | 38.5 | 16.5 | 21.5 | 508 | 36 | 170.2 | 55.0 |
| 17 | M | 44 | 47.5 | 3990 | 3097 | 84.0 | 65.2 | 1.29 | 25.8 | 65.0 | 21.4 | 39.2 | 390 | 35 | 180.3 | 86.4 |
| 18 | M | 70 | 37.6 | 3813 | 2032 | 101.4 | 54.0 | 1.88 | 16.9 | 51.5 | 23.5 | 34.6 | 532 | 32 | 172.7 | 75.0 |
| Mean | | 67.2 | 36.8 | 3533 | 2118 | 95.2 | 58.5 | 1.69 | 17.6 | 50.4 | 13.6 | 32.7 | 514.7 | 36.2 | 169.6 | 62.5 |
| SEM | | 2.7 | 1.8 | 236 | 89 | 2.5 | 2.1 | 0.11 | 0.7 | 2.4 | 1.6 | 2.0 | 22.1 | 3.3 | 1.5 | 2.8 |

TBW = total body water, $Na_e$ = total exchangeable sodium, $K_e$ = total exchangeable potassium, BCM = body cell mass, LBM = lean body mass, ECM = extracellular mass, Resist = total body bioelectrical resistance, React = total body bioelectrical reactance

What is claimed is:

1. A method for measuring certain ones of total body cell mass, total extracellular mass, total exchangeable potassium and total exchangeable sodium of a subject comprising the steps of:
   attaching an electrical impedance analyzer to a subject;
   introducing a high frequency, low amperage current from the impedance analyzer into the body of the subject;
   measuring the total body resistance and reactance of the subject; and
   determining the total body cell mass and the total extracellular mass by applying the measured total body resistance and reactance and the height of the subject to equations derived from multiple linear regression analysis of measured bioelectrical resistance and reactance of a selected test group of subjects.

2. The method of claim 1 wherein the total body cell mass and the total extracellular mass are determined according to:

$$BCM = \frac{16.4 + 0.61(Ht)^2/R}{3.4 + 34.8/X_c - 5.97 \times 10^{-5}(Ht)^2}$$

$$ECM = 16.4 + 0.61(Ht)^2/R - \frac{16.4 + 0.61(Ht)^2/R}{3.4 + 34.8/X_c - 5.97 \times 10^{-5}(Ht)^2}$$

where:
$H_t$ = height (CM)
$X_c$ = total body reactance (ohms)
R = total body resistance (ohms).

3. The method of claim 1 further including the step of calculating the total exchangeable potassium and the total exchangeable sodium of the subject according to:

$$K_e = \frac{1968 + 7.32(Ht)^2/R}{2.4 + 34.8/X_c - 5.97 \times 10^{-5}(Ht)^2 + 1}$$

where:
$K_e$ = total exchangeable potassium (mEq)
$H_t$ = height (CM)
$X_c$ = total body reactance (ohms)
R = total body resistance (ohms)

$$Na_e = \{1.87 + 34.1/X_c - 4.66 \times 10^{-5}(Ht)^2\}/K_e$$

where:
$Na_e$ = total exchangeable sodium (mEq)
$H_t$ = height (CM)
$X_c$ = total body reactance (ohms)
$K_e$ = total exchangeable potassium (mEq).

4. The method of claim 1 wherein the step of attaching an electrical impedance analyzer comprises the step of attaching a plurality of electrodes connected to a four terminal, phase sensitive, impedance plethysmograph to a subject.

5. The method of claim 4 wherein the electrodes are connected to the prominences of the radius and ulna, at the wrist and the distal metacarpals on one hand of the subject, and at the distal metatarsals and between the medial and lateral malleoli at the ankle of one foot of the subject.

6. The method of claim 1 further including the step of:
   determining the total exchangeable potassium and the total exchangeable sodium by applying the measured total body resistance and reactance and the height of the subject to equations derived from multiple linear regression analysis of measured bioelectrical resistance and reactance of a selected test group of subjects.

* * * * *